United States Patent
Mandecki (10) Patent No.: US 10,907,195 B1
(45) Date of Patent: Feb. 2, 2021

(54) DEVICES AND METHODS FOR ASSEMBLING EXTREMELY LONG DNA MOLECULES

(71) Applicant: PharmaSeq, Inc., Monmouth Junction, NJ (US)

(72) Inventor: Wlodek Mandecki, Princeton Junction, NJ (US)

(73) Assignee: PharmaSeq, Inc., Monmouth Junction, NJ (US)

(*) Notice: Subject to any disclaimer, the term of this patent is extended or adjusted under 35 U.S.C. 154(b) by 462 days.

(21) Appl. No.: 15/434,775

(22) Filed: Feb. 16, 2017

Related U.S. Application Data (60) Provisional application No. 62/296,015, filed on Feb. 16, 2016.

(51) Int. Cl.
 *C12Q 1/68* (2018.01)
 *C12Q 1/6806* (2018.01)

(52) U.S. Cl.
 CPC .................. *C12Q 1/6806* (2013.01)

(58) Field of Classification Search
 None
 See application file for complete search history.

(56) References Cited

U.S. PATENT DOCUMENTS

| | | | | |
|---|---|---|---|---|
| 5,552,278 A | * | 9/1996 | Brenner | C12Q 1/6862 435/18 |
| 5,942,609 A | * | 8/1999 | Hunkapiller | C12P 19/34 435/5 |
| 7,164,992 B1 | * | 1/2007 | Mulligan | G16C 20/10 702/20 |
| 2003/0054376 A1 | * | 3/2003 | Mullis | G01N 33/585 435/6.15 |
| 2008/0044862 A1 | * | 2/2008 | Schatz | C12N 15/1093 435/85 |
| 2015/0167066 A1 | * | 6/2015 | Link | C12Q 1/6844 435/6.12 |

OTHER PUBLICATIONS

Briggs et al. (Nucleic Acids Research, 2012, 40(15):e117, p. 1-10) (Year: 2012).*
Hastie et al. (PLoS One, 2013, 8(2):e55864, p. 1-10) (Year: 2013).*

* cited by examiner

*Primary Examiner* — Stephanie K Mummert
(74) *Attorney, Agent, or Firm* — Moser Taboada

(57) ABSTRACT

Provided among other things is a method of applying force to a macromolecule such as dsDNA to make an end more accessible, such as more accessible to ligation.

13 Claims, 4 Drawing Sheets

Fig. 4. Block diagram for the ligator.

DEVICES AND METHODS FOR ASSEMBLING EXTREMELY LONG DNA MOLECULES

This application claims the priority of U.S. Application No. 62/296,015, filed Feb. 16, 2016, the contents of which are incorporated herein in their entirety.

The present application relates generally to methods and devices for assembling long DNA molecules, in particular, long double stranded DNA molecules.

In recent years there has been a tremendous effort made to reduce both the time and cost to perform DNA sequencing. This has resulted in the generation and collection of huge quantities of data that have created new disciplines in health and life sciences. However, there has been far less attention paid to the area of DNA synthesis. The synthesis of artificial DNA is conducted with well-defined and reliable methods. However, the cost per base has not been reduced significantly, and there are improvements related to assembling larger constructs that are needed to realize the promise of synthetic biology. This situation (cost and technical issues) has slowed the growth synthetic biology and clearly needs to be addressed in order for the promises of molecular biology to be realized.

The solution to rapid and economical assembly of genes requires two solutions: (1) dramatically reducing the cost of synthesizing short oligo nucleotides; and (2) formulating protocols for rapid assembly of gene constructs and developing methods to transfer them into organisms. An important first step for this concept to produce extremely low cost oligonucleotides using PharmaSeq Inc.'s light-activated p-Chip microtransponders, as described in U.S. Ser. No. 14/972,659, filed Dec. 17, 2015. This method, which is known as "Sequence-directed combinatorial DNA synthesis" is being further developed under a SBIR grant from the National Human Genome Research Institute and is projected to reduce the cost of oligonucleotides significantly.

The main purpose of the current patent application is to provide instrumentation and associated products and methods to efficiently ligate long, double-stranded DNAs in the 10,000 bp to 100,000 bp (or higher) range, thereby addressing the assembly issue. A basis for achieving these products and methods involves the use of solid phase supports and sequential chemical ligation of shorter fragments to produce large DNA structures: genes and eventually chromosomes. The final products of the ligation can be transferred to living cells for expression of biological products. Appropriate metrics and analysis methods can be developed to identify and characterize full-length functional DNA constructs in cells. DNA sequence analysis can be performed to verify the integrity the DNA inserts. This platform technology lends itself to automation.

The technology yields instrumentation and associated reagents, experimental protocols, disposables, software and accessories. In addition, the technology offers the assembly of long genomic fragments as a custom service.

This patent application describes methods and instrumentation that will facilitate the construction of large scale genetic materials (genes and chromosomes) and their transfer and transformation into living cells. The work will greatly enhance the newly emerging field of synthetic genomics by providing molecular biologists and other scientists with robust tools that will enable them to develop products based on advances in genetics and understanding of DNA. These new methods will reduce costs and lower the time it takes to perform applied research in such fields as drug discovery, novel food crop design, animal husbandry and the treatment of disease.

SUMMARY

DNA assembly methods and devices, substantially as shown in and/or described in connection with at least one of the figures, as set forth more completely in the claims, are disclosed. Various advantages, aspects, and novel features of the present disclosure, as well as details of exemplary embodiments thereof, will be more fully understood from the following description and drawings.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

A goal of this patent application is to describe a new method for the assembly of extremely long double stranded DNA. Extremely long double stranded DNA (dsDNA) is defined as about 30 or about 50 kbp or more. These are assembled for example from "kilo-mers," which are defined as 632355-3 double stranded of about 1 kb to about 40 kb, preferably about 5 kb to about 20 kb. For example, assembly can be from about 10 kb DNA building blocks. The assembly can be transferred to living cells. The ability to reliably and inexpensively build large DNA constructs greatly facilitates the synthesis of complex genomic regions and, later, chromosomes.

There are four problems associated with ligation of long double-stranded linear DNA fragments.

First, as the length increases to about 10 kb and beyond, the DNA structure in solution resembles that of a random coil with a persistence length of about 50 nm. This means that both ends of the DNA fragment become increasingly buried inside the random coil, which results in both ends being relatively unavailable for ligation with other DNA fragments. If two similarly-sized fragments are involved, the probability of successful ligation becomes even lower since both ends are unavailable or only partially available.

Second, as the length and the molecular weight of the DNA fragments increases, the mobility of the DNA (and of both of its ends) is reduced due to lower diffusion rates. This, in turn, further reduces the ligation rate.

Third, as the length of the assembled DNA fragment grows, the total negative charge on the DNA random coil also increases. This leads to increased electrostatic repulsion of the ligation partner, and a reduced ligation rate.

Fourth, as the length of the DNA fragment increases, the volume occupied by the DNA random coil increases and the useful molar concentration of DNA is reduced. As a result, the probability of having two proper ends of the ligation partners in the same area is reduced, thus lowering the ligation rate.

Here we describe methods that counteract the effects summarized above by increasing the exposure of the end of the longer ligation partner, thereby increasing the efficiency of ligation. This is accomplished by attaching the other (non-ligating) end of the DNA molecule to a solid phase, such as a nano- or microparticle, and subsequently applying either an electric field, a magnetic field, or both, as needed. When an electric field is applied, the DNA is effectively stretched due to repulsive electrostatic forces acting on the negatively charged phosphodiester backbone, which, in turn, exposes an end for ligation. If a magnetic field is applied, a magnetic bead moves through the solution, which stretches DNA due to hydrodynamic forces.

Some of the discussion below is framed in terms of a preferred embodiment, namely the use of nanoparticles. In all cases, a particle solid phase can be used.

Figure 1:
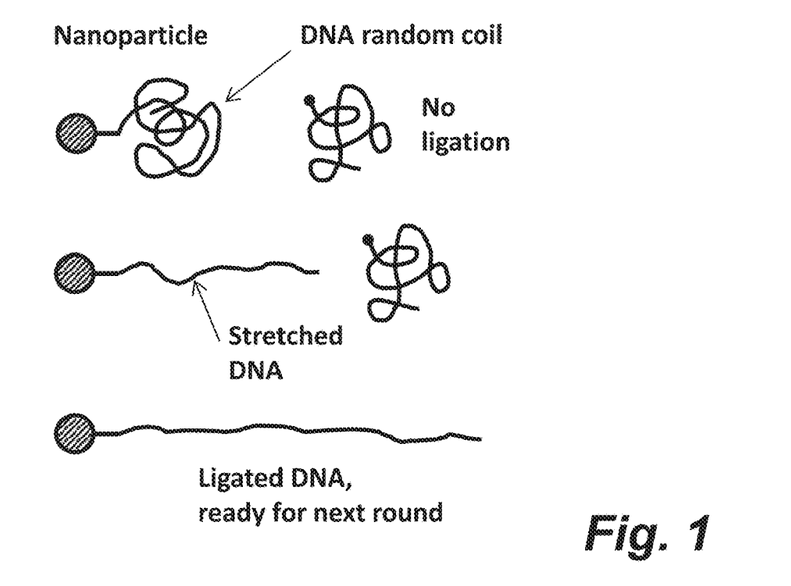
FIG. 1 schematically shows a DNA ligation according to the invention.

A exemplary assembly of 100 kb DNA from ten 10 kb fragments is done in a series of ten ligations as follows (FIG. 1). First, DNA Building Block 1 is immobilized on a solid phase. Then, an electric field or magnetic field is applied and the DNA is stretched. This exposes one end of the DNA molecule. DNA Building Block 2 is then added together with the DNA ligase and the two DNA fragments are ligated. The resulting ligation product (linked Blocks 1 and 2) is stretched by the electric/magnetic field, and Building Block 3 is added. This process is repeated until all ten building blocks are sequentially assembled. Appropriate restriction enzymes that produce non-palindromic overhang sequences, such as class IIs enzymes, can be used for creating unique protruding DNA ends for each fragment; thus there is no possibility of a block ligating to itself or to an undesired byproduct of the ligation. When the ligations are completed, the DNA construct is transferred to cells using for example electroporation. A "Non-Interfering" or "NInf" restriction enzyme is one that can create a non-palindromic overhang, and can create an overhang that, for one of the cleaved ends, can be annealed to a dsDNA such that the cleavage recognition sequence is not re-created. Examples include Class IIs enzymes, such as are described in more detail below. With Class IIs enzymes, the cleavage sequence is outside the recognition sequence, such that one cleaved end does not have associated recognition sequence.

Some restriction enzymes, like BsaXI, excise the recognition sequence. Some restriction enzyme recognition sequences can be engineered to include further restriction sites, that can be used, by sequential addition of the further restriction enzymes, to render the residual segments with potentially interfering overhangs practically unligatable.

The Building Block can be introduced into the reaction mixture as a vector from which the Building Block is excised. A vector defined as a biologically replicable DNA, such as a plasmid or viral DNA.

For the Building Block vector, a close to 10 kb sequence can be flanked by two restriction sites recognized by the class IIs or similar enzymes. There are no other sites of that type within the sequence of the internal region. Examples of such enzymes are BsaI or BbsI; they recognize a 6 nt DNA sequence and produce a 4 nt long 5' overhang. The sequence of the overhangs can be designed such that no two overhangs among the ten building blocks have the same sequence. Because of that feature, no ligation is theoretically possible other than the ones that are desired. One exception is allowed in cases where the circularization of the assembled fragment is desired. In this situation, the class IIs enzyme can create overhangs with the same sequence for the cut that is most proximal to the solid phase and the cut that is most distant.

There are three elements that can further contribute to the here-described advancement of the ligation methodology: (1) one end of the typically longer (and more difficult to deal with) ligation partner is exposed for the ligation reaction via the application of an electric or a magnetic field; (2) the length of the typically smaller ligation partners (which can be sequentially added) is relatively kept constant so that their DNA ends are available for ligation, at least to a significant extent; and (3) the movement of the ligation product in the reaction volume can be controlled during the course of ligation by applying an electric or magnetic field.

This method can be implemented using inexpensive hardware components. Further automation can be effected, including using standard laboratory robots for pipetting of the reagents.

Notable features that can be provided with the assembly method are one or more of the following TABLE:
• No pipette of linear or assembled DNA.
• No reagent addition during assembly (except possibly for source of the added segments, such as supercoiled plasmid DNA).
• No moving parts.

A system for conducting the method can include a special test tube ("L-tube") for applying an electric and magnetic field and a special instrument, a "ligator", which provides electrical power to control the electric and magnetic fields, houses the L-tube, and has solenoids to control the magnetic field. The ligator instrument and its functions can be computer-controlled.

When the product DNA is transferred to a living organism, the integrity of the DNA can be established for example by biological selection or screening for proper biomarkers, by q-PCR and by DNA sequencing.

Model for Ligation Rate of Long DNA Fragments

In this section we present a functional analysis of the kinetics of the ligation process. Let's consider length dependencies for the ligation of two double-stranded DNA fragments both of length L, where L>>persistence length. (In this context we define persistence length as the length at which the time-average angle made between the two ends of an intrinsically straight DNA molecule is equal to one radian, or 57° [1]. The persistence length of the supercoiled DNA is ~100 nm, being twice the value of the persistence length of the double-stranded linear DNA, ~50 nm [2]).

The ligation rate can be roughly proportional to the collision rate of the ends of different DNA molecules. For each end, the collision frequency can be proportional to the product of the solvent exposure factor (S) of the end (for large DNA, the ends tend to be hidden in the random coil formed by the DNA) and the diffusion constant (D). S is proportional to $L^{-1/3}$, and D for many polymers is also approximately proportional to $L^{-1/3}$. Thus, the likelihood of an end to collide can be proportional to the product of S and L, i.e., $L^{-2/3}$. The ligation rate can be enhanced by increasing the DNA concentration; we will assume that practical limit for the DNA concentration here does not depend on DNA length. Thus, the longer the DNA, the lower the molar 632355-7 concentration of DNA in the ligation reaction. This adds a multiplicative term, $L^{-1}$, to the expression for the contribution of one DNA molecule to the ligation rate, leading to a dependence on the $L^{-5/3}$ factor. The actual ligation rate can be proportional to the square of this term (because two molecules [two ends] participate in the ligation), hence:

Ligation_rate~$1/L^{3.3}$

The dependence means that, as the length of a DNA molecule increases by a factor of 10, the ligation rate will decrease by a factor of ~$2\times10^3$. This significant reduction can make ligations inefficient and cloning of the ligation product very difficult.

Let's now discuss how the estimated ligation rate will change as a result of stretching of DNA bound to a solid phase. Regardless of the length of the ligation product, the contribution of one DNA end to the ligation rate would be approximately constant, since the bundled stretched ends of DNA molecules bound to the solid phase all would behave in the same way from the perspective of the incoming, second DNA molecule. In the method, the length of the DNA molecule being ligated to the stretched ends is always the same (this molecule is one of ten Building Blocks). Thus, the ligation rate would not change as the DNA is grown on the solid phase.

This model idealizes molecular ligation processes. Only approximate functional relationships are described above. The electrostatic repulsion between DNA molecules being ligated and entropic effects are not included; its inclusion would make the dependence even more pronounced.

Stretching Long DNAs as Means of Accelerating Ligation Rate

A focus of this patent application is the proposition that changing the structure of long DNA fragments in solution (by stretching DNA to increase the exposure of DNA ends to other DNA molecules) will accelerate ligation reactions. Stretching would cause the DNA molecule to resemble a long rod with its ends fully exposed, similar to what is observed with much shorter molecules that undergo efficient ligation. Thus, Applicants have deduced that so stretching of DNA molecules increases ligation rates.

Stretching of DNA is commonly done in other contexts in everyday experiments in molecular biology laboratories. Gel electrophoresis of DNA is the most common example. To penetrate the pores in a gel, DNA gets squeezed and stretched so that it can undergo reptation, while being pulled and pushed by an electrical field. Stretching of single molecules of DNA has been thoroughly investigated as well. In a typical experiment, two nanoparticles are attached to the DNA ends, held optically through the interaction of the nanoparticles with a laser beam, and the DNA is analyzed for mechanical and other properties.

The current method can use one or more of that in the following TABLE to effect the stretching:
 () Applying an electrical field to DNA. The negatively charged phosphate groups are attracted to the positive electrode. A convenient approach is to attach the DNA molecule to solid phase, such as a nano- or microparticle (a bead), and apply an electric field.

(2) Pulling through solution a magnetic bead to which DNA is attached. The movement of DNA in a buffer will generate a shear and the hydrodynamic interactions that will result in at least a partially stretched DNA conformation. The magnetic bead will move as a result of generating a magnetic field near the sample tube.

A combination of (1) and (2) is also possible. In this configuration, magnetic beads are used to bind the first DNA building block, and the magnetic field is used primarily to counteract the electric force that not only stretches DNA but also moves DNA in the tube (similarly to the DNA movement in electrophoresis). In addition, the magnetic force can be used to mix the beads in the buffer and to collect beads and DNA on the test tube wall between the ligation steps and before electroporation (if needed).

Choice of Solid Phase

Overview. If an electric field is applied to stretch DNA, the main purpose of solid phase is to provide a "counterweight" or an "anchor site" that restricts the movement of the DNA, allowing it to be stretched. Without an anchor site, the DNA random coil would simply move in the direction of electric field. The anchor can be as small as possible (but effective for stretching DNA) so that the maximum possible packing of DNA molecules in a given volume can be attained. The goal here is to obtain a final ligation product at a sufficient yield for successful transfer into a cell. An amount commonly considered adequate for transformation into yeast is 1-100 ng of DNA, which for a 100 kb DNA fragment contains $10^6$ to $10^8$ molecules.

Gold Nanoparticles.

Gold nanoparticles, because of their high density, low reactivity and ready commercial availability of different sizes and coatings, are a suitable solid phase for this application. Several sizes can be used, for example of size ranging from 10 nm to 1 µm in diameter, such as 20 nm size. A gold nanoparticle of such a size has a molar mass of $50\times10^6$ daltons, which is close to 10-fold greater than that of 10 kbp DNA ($6.5\times10^3$ daltons) and is similar to the molar mass of a 100 kbp DNA. The surface area is 1,200 $nm^1$. This size seems to be a proper starting point for exploring the effectiveness of the method of the invention, and such nanoparticles are commercially available as streptavidin-coated particles. Available concentrations of gold nanoparticles are easily in the $10^{12}$ particles/mL range, sufficient for the task. (These particles can be magnetic.)

In the case of a 10 kb fragment of DNA, a random coil will have a diameter of 250 to 300 nm. When attached to a gold nanoparticle, it will stretch to its full length of around 3,400 nm. As an analogy consider a piece of rope that is 3.4 meters long and 2 mm in diameter. If it forms a tight, random coil, the diameter can be about 30 cm. However, if it is attached to a ball that is about ten times the total mass of the rope, then it will stretch to its full length as the proper force is applied.

Magnetic beads.

The use of magnetic particles, which are available in many sizes, from 5 nm to many microns, offers the advantage of being able to manipulate the DNA-bound particles with both electric and magnetic fields. Applying a magnetic field (for example, a linear gradient) will result in the particle moving in the direction of the gradient, dragging the bound DNA and stretching it due to hydrodynamic effects.

Ligation product enrichment. Under proper conditions, the application of an electric field to the full-length DNA construct attached to a magnetic bead can counteract the motion caused by the magnetic field and keep the particle (and the DNA) stationary. Let's assume that only one DNA construct is attached to the particle, which can be readily achieved if, when the DNA is being linked with the nanoparticles, the number of DNA molecules in the L-tube is smaller than the number of particles. In this situation, incomplete DNA constructs that are shorter than the full-length DNA move in solution, and as such they can be forced to be deposited on the wall of the L-tube while the full-length DNA is stationary in solution. This enables a very convenient procedure to enrich the ligation product in full-length DNA and is one of the reasons why the use of both electric and magnetic fields can be desirable. (We assume for the sake of this illustration that the beads are uniform in size.)

Instrumentation and Disposables

Figure 2A:
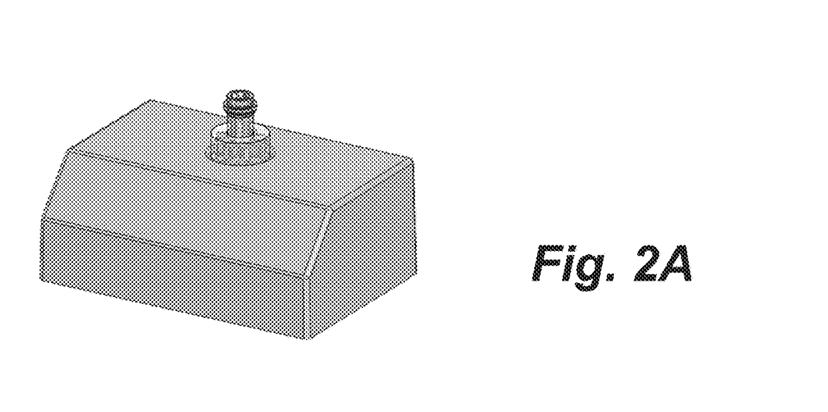
FIG. 2A shows an exemplary ligator.

Both the electric field and magnetic field can be generated by a new instrument, a "ligator" (FIG. 2A). To conduct a ligation reaction, a specially designed test tube (an "L-tube") is placed inside the instrument. The ligator can for example have a two-channel (power for the electrical and magnetic steering of nanoparticles), eight- or 32-position (per channel) switching power supply. The voltage and power for each position and each channel can be computer controlled.

The instrumentation described here can have a controller 150 (illustrated in FIG. 2B), which can comprise a central processing unit (CPU) 154, a memory 152, and support circuits 156 for the CPU 154 and is coupled to and controls the ligator (electrodes, solenoids, etc.) or, alternatively, operates to do so in conjunction with computers (or controllers) connected to the ligator. CPU 154 may be realized as a general purpose CISC, RISC or other traditional microprocessor architecture, or it may be realized as a FPGA.

Figure 2B:
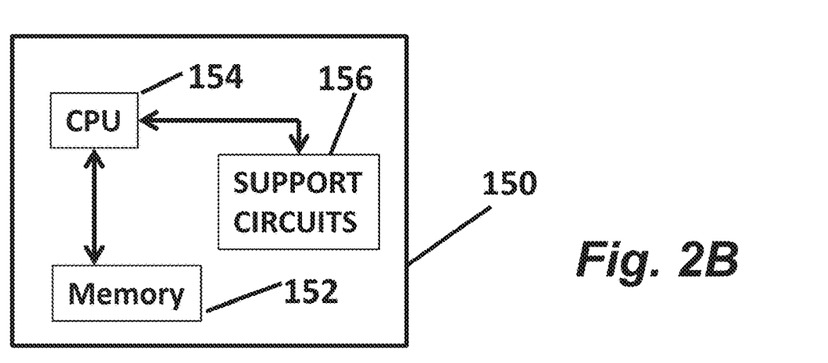
FIG. 2B shows an exemplary controller for a ligator.

For example, another electronic device can supply software, or operations may be calculated off-site with controller 150 coordinating off-site operations with the local environment. The controller 150 may be one of any form of general-purpose computer processor, state machine, or an array of processors, that can be used for controlling various devices and sub-processors. The memory, or computer-readable medium, 152 of the CPU 54 may be one or more of readily available memory technologies such as random access memory (RAM), read only memory (ROM), flash memory, floppy disk, hard disk, ReRAM, magnetic memory, or any other form of digital storage, local or remote. The support circuits 156 are coupled to the CPU 154 for supporting the processor in a conventional manner. These circuits can include cache, power supplies, clock circuits, address decoders, input/output circuitry and subsystems, and the like. Methods of operating the synthesizer may be stored in the memory 152 as software code that may be executed or invoked to control the operation of the synthesizer. The software may also be stored and/or executed by a second CPU (not shown) that is remotely located from the hardware being controlled by the CPU 154. While the above discussion may speak of the "controller" taking certain actions, it will be recognized that it may take such action in conjunction with connected devices with computation power.

L-Tube.

Figure 3A:
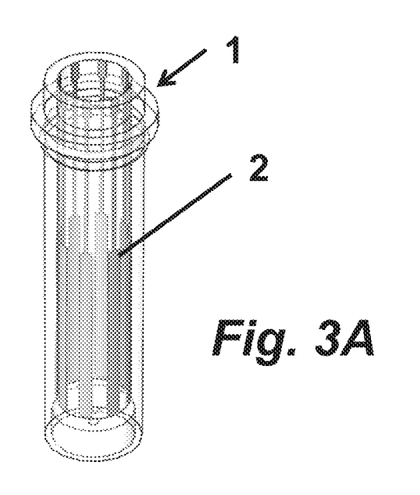
FIG. 3A shows an exemplary L-tube with electrodes 2.
Figure 3B:
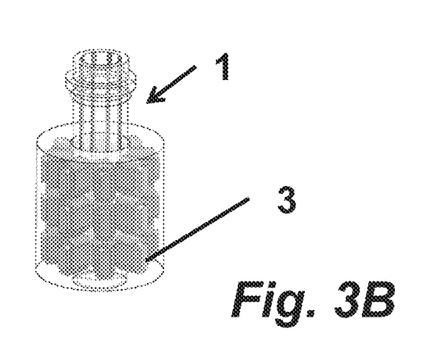
FIG. 3B shows an exemplary L-tube with solenoids and/or electromagnets 3.
Figure 3C:
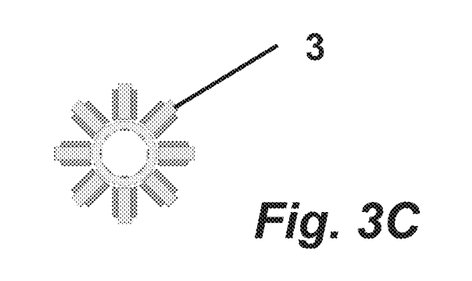
FIG. 3C shows exemplary solenoids from a bottom view.

The L-tube can be made for example of polypropylene or glass, and the working part (in ligations) can have, for example, a ~10 mm internal diameter and is ~10-20 mm high (FIG. 3). (FIG. 3A: L-tube 1 with electrodes 2; 3B: L-tube with solenoids/electromagnets 3; 3C: solenoids 3—bottom view.) The internal wall of the L-tube is lined for example with multiple (e.g., eight) vertical gold-coated aluminum electrodes connected by eight wires to the power supply. The total length of the L-tube can vary, for example from less than 10 mm to 30 mm or more. The electrodes generate an electrical field between them. The direction of the field can be changed (e.g., rotated) depending on the electrodes to which voltage is applied.

An application of voltage to two electrodes on opposite sides or near opposite sides of the L-tube will cause a long DNA fragment attached to the nanoparticle to stretch, and the DNA-nanoparticle assembly will start to move. Periodic voltage changes, several times a second or every few seconds, can cause the DNA-nanoparticle assemblies to move along a circular trajectory, the diameter of which is on the order of tens or hundreds of microns, but the average position of the center of the trajectory will stay the same. This implies that the local concentration of the reagents will not change. To increase the uniformity of the electric fields, different voltages can be applied to more than two electrodes at a time.

A thin sheet of aluminum may for example be used to build the electrodes (FIG. 3). The electrodes can be coated for example with a thin layer of gold (nanometers thick) to make them chemically inert. The electrodes can be fixed in place using flexible plastic rings inside the L-tube. Although the long-term goal is to make the L-tubes and the electrodes disposable, initially they can be reused. Eight wires can be separately connected to the electrodes by soldering. If needed, a smaller or larger diameter L-tube can be made. After the ligations are completed, the assembled DNA can be gently transferred to the electroporation cuvette (widely available commercially) for insertion into living cells.

A regular 3-5 mL round polypropylene test tube can be adapted by inserting a gold-plated electrode and securing it with plastic O-rings. Approximately 20 electrodes can be made from aluminum and gold plated. The electrodes can be reused. Insulated metal wires can be soldered to the top section of the electrodes and run to the ligator. Alternatively, a plastic clip can be designed and built to electrically connect the electrodes to the ligator.

Finite Element Method electromagnetic field solvers, such as FEMM (www.femm.info), can be used to estimate the static electric and magnetic fields within the L-tube for various electrode and magnet geometrical arrangements and excitations, and for L-tube contents with the dielectric and conductive properties being studied.

The electrodes can be fabricated using conventional flex circuit technology. A thin flexible rectangular substrate of polyimide (~100 micrometer thin), on which copper electrodes plated with gold are printed on a wide strip, can be rolled to fit the interior of the L-tube. A narrow neck of this flex circuit carrying conductive traces from each electrode, can extend up through the L-tube's top to either solder pads or a rigid edge connector accessible from outside of the vial.

Application of the Magnetic Field.

The same L-tube can be used to apply a magnetic field when magnetic particles (e.g., nanoparticles) are used. The proper field gradient can be provided by either a small permanent magnet (as can be used in the case in magnetic separations) or can be generated by electrical current in a metal coil(s) with for example a ferrite core placed adjacent to the L-tube (FIG. 3). An illustrative series of vertically arranged vertical coils is shown in FIG. 3; the purpose is to have the option of moving particles in the up-and-down direction as well. The application of the magnetic field will cause the DNA-magnetic particle assembly to move toward the coil. If multiple coils are placed around the L-tube, it is possible to move the DNA-magnetic particle in a circular trajectory, the diameter of which is on the order of tens of microns or hundreds of microns, or even in three dimensions (defined as the volume occupied by the solution) as desired, at the same time stretching the DNA.

Application of Both Electrical and Magnetic Fields.

If both an electrical field and a magnetic field are applied properly to a DNA-magnetic particle in the L-tube, the position of the particle in a horizontal plane and in the direction in which the DNA points, as well as the speed of the particle, can be controlled. In a particular scenario, when the magnetic force and electric force are equal but pointing in opposite directions, the DNA-particle can be stationary and the DNA can be stretched. Interestingly, the net force acting on shorter DNAs on particles (truncated and incomplete products of the ligation) will not be zero under the described conditions. Such DNAs can be removed from the solution (e.g., deposited on the wall) by a prolonged exposure of the particles to the two fields. The field strengths can be adjusted with each ligation step to provide such collision for the shorter products, but not DNA being ligated.

Ligator.

Figure 4:
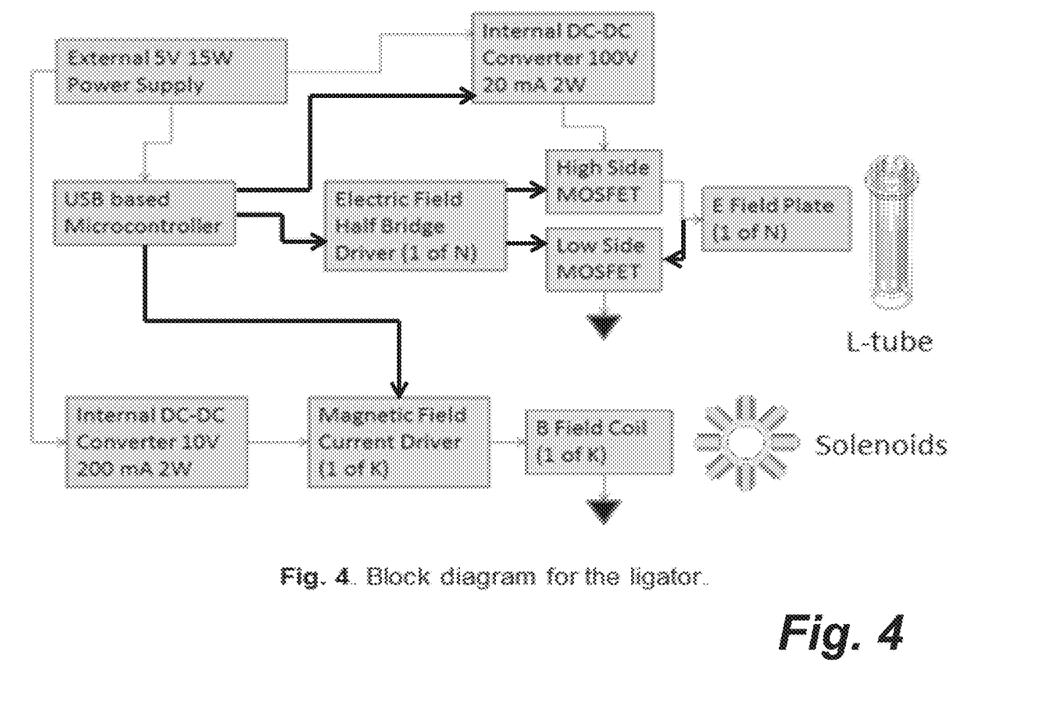
FIG. 4 shows exemplary components of a ligator.

The ligator provides electrical power for steering of particles with electric and magnetic fields, setting the magnitude and direction of each field in one of for example eight zones using computer control. The electric field source applies for example in embodiments at most 100 V and 10 mA (1 W max) between two opposed electrodes. The magnetic field source applies for example in embodiments at most 10 V and 100 mA (1 W max) to three zone magnets. Only a small fraction of this power will normally be dissipated in the sample cell, less than 100 mW total. FIG. 4 shows example components (power paths in thin lines, control lines in thick lines). A low-voltage external power supply drives internal converters to generate 10 V or 100 V. These are switched to zone outputs via H-bridges or linear mode MOSFETS. Many existing commercial devices can be adapted to implement these two types of sources. For example, for the electric field, a stepper motor controller IC can switch 3 outputs to ground or 200 V at 1 A, with integrated thermal and overcurrent protection, suitable for the electric field source. Enabling the high side of one (see FIG. 4, block diagram) and the low side of another (not shown) would energize two opposing plates. The 100 V converter can be adjusted to a lower voltage to change the electric field strength. For the magnetic field, a voice coil driver or fan motor controller is adequate. In internal DAC controls a linear mode MOSFET to adjust the current over a 0 to 100 mA range. All of these devices can regulate both the electric and magnetic field at any frequency in the expected range, starting with extremely low (one switch per hour) up to 1000 Hz or even faster.

The temperature of the L-tube placed in the ligator can be controlled. Control can be subject to feedback regulation from the controller in conjunction with appropriate one or more sensors. This can be useful for example if temperature cycling is used. Temperature control can be done for example by placing the unit in the incubator or cooler/refrigerator, adding a Peltier device, recirculating a coolant, electric heating and the like.

Examples of Suitable Parts.

External power supply (12 V, 18 W) can be provided by ICCNexergy, Inc. (FW1812-760F), and a stepper motor controller IC can be a Sanken SX68001MH. Voice coil and fan motor controller IC can be obtained from Linear Technology (LTC1695). If needed, or as a control, a typical cylindrical permanent magnet of the required size can be 5 mm diameter, 3 mm length, Radial Magnet, Inc. Model 8017, 5000 gauss (0.5 Tesla). An equivalent electromagnet wound on a 3 mm diameter iron core uses 120 turns at 50 mA (hyperphysics.phy-astr.gsu.edu/hbase/magnetic/solenoid.html#c3). The winding resistance with 30 AWG copper wire is about 1 ohm, and 50 mV and 3 mW would be needed to drive the current.

In addition, a commercially available electroporator with electroporation cuvettes can be used to transfer DNA to a cell.

Figure 5:
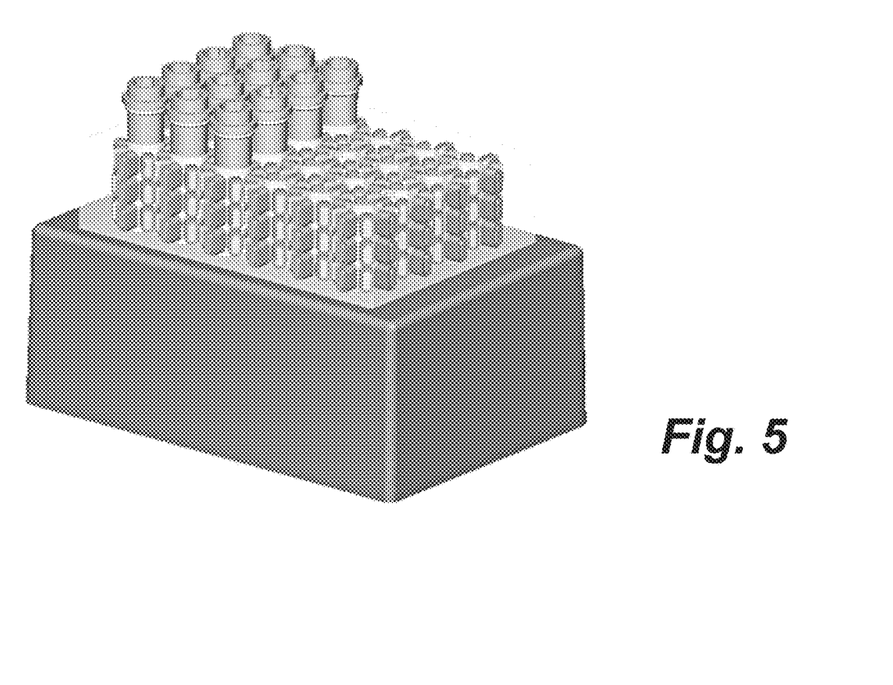
FIG. 5 shows a multi-ligation site ligator.

A disposable multi-well ligator plate can be constructed. A compatible ligator instrument can also be built. Both are represented in FIG. 5. For example, the system can allow 12 to 24 simultaneous, complex ligations per plate to be conducted. Of course, with proper robotic instrumentation (plate handlers and pipetters commonly used in high throughput screening assays), many plates can be processed in parallel.

Homogeneous Reaction and Transfer Protocol

The term "homogeneous ligation reaction and transfer" refers to a protocol that facilitates assembly of a full-length ligation product and transfer of the assembled DNA to a cell in a simple procedure without processing samples using separation or washing steps. In embodiments, the protocol does not involve pipetting of any DNA other than supercoiled vector DNA carrying the Building Blocks (e.g., kilo-mers).

Figure 6:
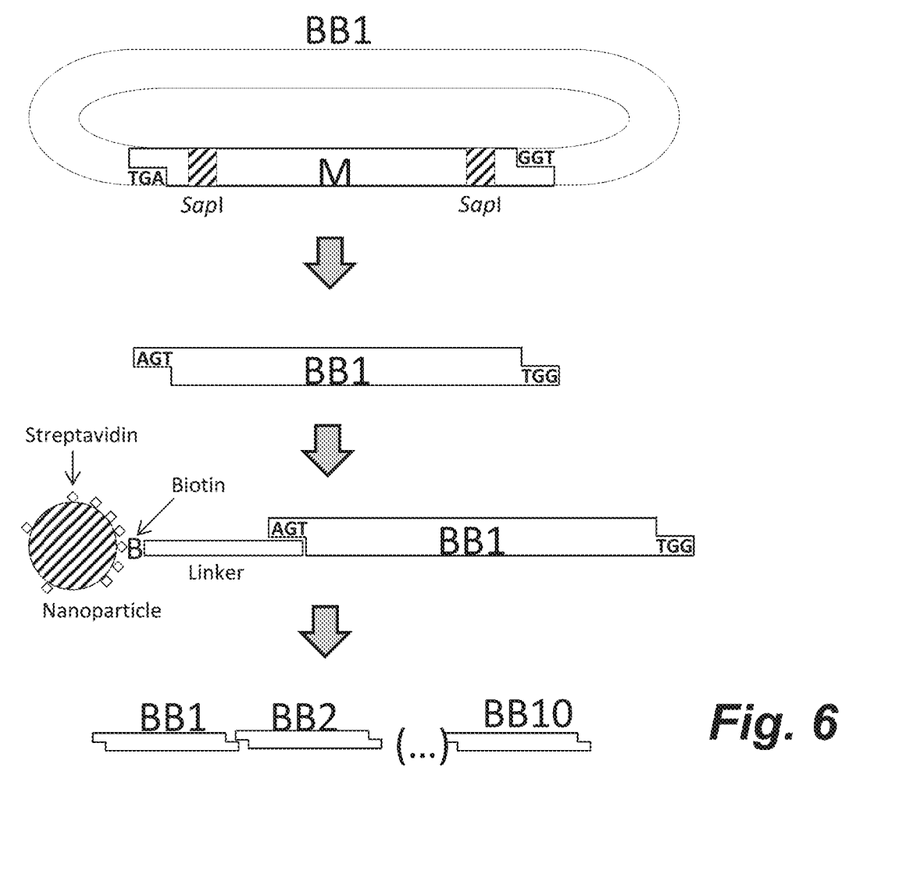
FIG. 6 shows an exemplary strategy for ligating large DNA blocks.

The strategy for assembling the Building Blocks into for example 100 kb fragments (FIG. 6) can utilize incorporating exactly two class IIs restriction sites (e.g., SapI) into the vector that carries a given Building Block. The SapI enzyme cleaves the following sequence:

GCTCTTCN↓NNN
CGAGAAGNNNN↓-5' creating 3 nt long 5' protruding ends. The cleavage does not depend on the protruding sequence, thus each Building Block can have unique protruding ends. They are unique in a sense that each ligation step involving the Building Blocks uses two unique complementary ends. This assures that the ligation of ten Building Blocks can proceed in accordance with only one pre-planned assembly scheme.

There is no dependence of the assembly process on the sequence between the two Class IIs cleavage sites in the maintenance plasmid as long as there are no internal sites. SapI sites, for example, are rare in DNA; their expected frequency is one per $4^7$ bp, i.e., once every 16,384 bp in random sequences (if the frequency of each nucleotide is 25%). The presence of the native SapI sites can be dealt with by modifying the current ligation method such that no SapI restriction endonuclease is present in the ligation mix. In certain applications, SapI sites can be edited out of the sequence being assembled. On average, one edit would be needed per 16,384 bp. For coding sequence, editing can avoid changing the coded sequence.

Exemplary Ligation Procedure

The assembly can start for example by adding to an L-tube that in the following TABLE:
- Gold nanoparticles with an attached (for example through biotin-straptavidin interaction) double-stranded ~1000 bp DNA linker (to start the assembly process)
- SapI nuclease
- DNA ligase The electric field is applied for example at the start of the assembly and remains on during assembly. Then, in Step 1, supercoiled plasmid with Building Block 1 is added to the test tube. Once the plasmid is digested with SapI, Building Block 1 is ligated to the linker and connected to the nanoparticle. In Step 2, a second supercoiled plasmid with Building Block 2 is added to the reaction tube. It gets digested with SapI, and the protruding DNA end complementary to the protruding end of Building Block 1 gets ligated. The procedure is repeated with plasmids carrying Building Block 3 and higher until the full assembly of the 100 kb fragment is completed. Per design, the ligated DNA cannot be recut with SapI (as is the case with many restriction enzymes), since the SapI sites are not included in the assembled DNA as a result of the initial cleavage and ligation.

The final products in the test tubes are the long fragment itself as well as the shorter pieces (replication origin) from the maintenance plasmids (or other vector). The shorter pieces do not ligate to themselves since the DNA end sequences are not complementary.

In this scheme, the undesired religation of the two DNA fragments (a Building Block and a short DNA fragment carrying the maintenance sequence) to recreate SapI sites may occur; however, such sequences can be cleaved with SapI (provided in the reaction mixture). Nevertheless, the ligation reaction to form the long 100 kb fragment is driven to completion as properly formed DNA cannot be cut with SapI.

Alternative Ligation Schemes.

While the primary approach is the successive ligation of ten Building Blocks to a particle, other schemes are possible as well. One possibility is a "pyramidal" ligation scheme in which all Building Blocks are linked to nanoparticles according to a special pattern. Building Blocks are grouped into pairs, where for example the 3' end of the first block of the pair is linked to the nanoparticle, while for example the 5' end of the second block is linked to another nanoparticle. In the ligator, the DNA of both blocks is stretched and ligated, leading to a double-size DNA block carrying two nanoparticles on its ends. If one of the two particles is removed with a restriction enzyme (or using a different method), the double-sized block can participate in a ligation reaction with another double-sized block. The process continues. The length of the assembled DNA grows in an exponential fashion, increasing by a factor of 2 after each ligation round. The advantage here is that all DNAs participating in ligations are stretched. A mixture of this approach and the one described above can be used.

In addition, ligation schemes according to which multiple Building Block are simultaneously added to the L-tube are contemplated.

Enhancements to Ligation Methodology.

Additional steps can include introducing small DNA binding protein with low sequence specificity (such as histones or recA) to the reaction mix. This could favorably affect the DNA structure due to the effective shortening of the extended portion or balancing of the electrical charges involved.

Ultrasonic Exposure.

In addition, mild ultrasonic exposure (using a carefully chosen sound frequency and intensity) can be used to compensate for reduced diffusion rates.

Option to Form Circular Construct.

To circularize the obtained construct, a homing endonuclease site is included at the 5' and the 3' end of the designed 100 kb sequence, and this exonuclease used to cleave DNA. If needed, the enzyme is then removed from the ligation mix (e.g., by heating). The construct is then ligated.

Transfer Procedure.

After the reaction is completed, the ligation mix is gently moved to an electroporation cuvette, 1 mL of electroporation-ready cells is added, and electroporation is performed. The contents of the cuvette are then transferred to growth medium, and the culture is grown under standard conditions.

We assume that the nanoparticles will not be toxic to the cell. If they are, the nanoparticles can be removed by cleaving DNA with a restriction enzyme and removing the particles using a form of mild precipitation. In embodiments, it can be useful in such situations to use for example larger nanoparticles or microparticles.

Extension of the Assembly Procedure to DNA Constructs Longer than 100 kb.

DNAs much longer than 100 kb could be assembled using the method outlined here by combining two or more extremely long dsDNAs (e.g., 100 kb fragments). Because the assembly can be designed to proceed in the 5'-3' or 3'-5' direction, one can for example assemble one of two 100 kb neighboring fragments in the 5'-3' directions, and the other fragment in the 3'-5' direction. When done, one mixes the two reactions (that include two 100 kb DNAs on nanoparticles) and continues using the ligator instrument described above. It is believed that DNA constructs longer than 1 Mb can be made using this method.

Derivatizing Particle with Linker DNA

Proper solid phase derivatization and a proper start of the assembly process are needed for successful assembly. One approach is to attach a double-stranded or single-stranded DNA linker to the particle via the biotin-streptavidin interaction first, and only then to ligate Building Block 1. To accomplish this, either gold particles or magnetic particles precoated with streptavidin can be purchased from a commercial source. The linker DNA can be synthetic DNA 50-100 nt long labeled with biotin on its 5' end. This provides sufficient spacing of the initial 10,000 bp DNA ligation Building Block from the surface of the solid phase. The oligonucleotide(s) can be obtained from a commercial source. The linker is attached to streptavidin on the surface of the nanoparticle. The number of DNA molecules per particle can be determined by agarose gel electrophoresis [5].

Experiments are performed by ligating different length ssDNAs (500 bp to 10,000 bp range) to the linker-nanoparticle assembly. In these experiments, the DNAs can be fluorescently labeled during PCR. The amount of fluorescence that can be centrifuged into a pellet with nanoparticles can be measured.

Analysis of the Movement of DNA-Particles in Electric and Magnetic Fields

The analysis can be based on observing the accumulation of the particles (with or without DNA) on the L-tube wall (magnetic particles) or electrodes (gold particles) for example either by observing color or fluorescence. Migration rates on the order of 10-100 um/sec, comparable to diffusion rates, are expected.

Ligation Assay

The purpose of this assay is to measure the efficiency of ligation in a model system. For example, two 10 kb long DNA molecules are used; the DNA fragment of the first type is linked to gold particles (or magnetic particles), whereas the second type is provided either as a supercoiled or linear (cut with a restriction enzyme) structure. After ligation of the DNAs is completed, the efficiency is determined by adding to the mixture a short oligonucleotide labeled with a fluorescent dye; this oligo is ligated to the free-floating DNA end of the ligated assembly of two long DNAs, effectively tagging the solid phase in the assay with a fluorescent label. The amount of fluorescence is measured after depositing solid phase together with the ligated DNA on the wall or bottom of the test tube by gentle centrifugation or by an application of electrical or magnetic field, and then washing.

The unligated fluorescent short oligonucleotide will not be deposited on the wall or bottom of the test tube.

This fast assay can evaluate the intensity of the electric/magnetic field needed, the rate of change of the field intensity, the need to rotate the tube, optimal concentrations of the reagents, the most effective size of nanoparticles, and other parameters.

Ligation of Building Blocks to Form 100 Kb Constructs

Ligations can be done for example in the L-tube placed in the ligator instrument. For example, approximately $10^{10}$ nanoparticles derivatized with a linker can be used. Both the ligase and SapI can be added to the L-tube. The reactions will start with an addition of supercoiled plasmid DNA carrying Building Block 1. The reaction is done under conditions where either a rotating electric field or magnetic field is applied. The reaction continues for minutes to an hour. Next, plasmid DNA carrying Building Block 2 is added. Reactions continue sequentially with consecutive Building Blocks.

Release of Assembled DNA by Cleaving with Restriction Enzyme (if Needed) and Circularization The next key step can be to release the DNA fragment from the nanoparticle. This can be done for example by cleaving DNA close to its base with for example a class IIs restriction enzyme. The cleavage sequence is built into the sequence of the oligo immobilized on the nanoparticle.

The last and optional step can be to circularize the obtained linear e.g. 100 kb DNA fragment. A benefit is that the non-ligated DNA (presumably the DNA that did not undergo one of e.g. nine ligation reactions) could be digested with an exonuclease. This can greatly improve the yield of properly assembled DNA after cloning in yeast.

Transfer of the 100 kb Ligated DNA Fragment into Live Cells

The ligated DNA constructs are transferred to live cells through one of established methods, such as electroporation, transfection or injection. Types of live cells include bacterial cells (such as *Escherichia coli*), yeast cells, mammalian cells, plant cells, and other types. The characteristics of the transfer method can be determined, including those in the following TABLE:
- Total number of colonies obtained from the transformation
- Number of clones obtained per nanogram of assembled full-length DNA used in the transformation
- Number of clones obtained per nanogram of total DNA used in the transormation
- Fraction of clones having proper organization (order and approximate length) of the assembled DNA fragment
- Fraction of clones with the proper (expected) sequence of the assembled DNA fragment
- Ligation time
- Efficiency of an individual ligation step (% of fragments being built that underwent a successful ligation at that step)
- The dependence on the step number in a sequence of ten ligation steps Misc. Issues In the basic approach, only one of two DNA molecules being ligated is stretched. Of concern is the extent of exposure for the proper end of the unstretched molecule. In embodiments, the length of unstretched Building Blocks has been limited to about 10 kb or less. If in certain embodiments it is observed that ligations do not proceed as anticipated, then shorter lengths could be used.

It is expected that it will take from 10 ms to several seconds to stretch DNA in the ligation experiments. This estimate is based on the fact that during PFGE the electric field is changed at intervals starting from 50 ms and higher (Bio-Rad CHEF Mapper XA system) for DNA lengths up to 10 Mbp. The relaxation time of T4 DNA (170 kb long) in an extended conformation is on the range of 0.2 s to 0.7 s [6]. Generating electrical voltage changing at 100 Hz or slower can be done using the approach described above.

Diffusion of biomolecules in solution is well understood [7]. The average diffusion speed is a function of the mass of the molecule and can be readily calculated [8]. For example, the diffusion time for a 1 kb long DNA molecule to move over a distance of 1 µm is 0.4 s.

It is currently routine to construct 10 kb inserts in *E. coli* plasmids with 100% sequence accuracy; several commercial sources provide such a service. The question is whether the proposed assembly method will impact the DNA sequence accuracy after the assembled DNA is transferred to a cell. In embodiments, we chose not to use PCR because a significant rate of sequence errors due to PCR would be unavoidable. In embodiments, we also chose supercoiled plasmid DNA as the starting material to avoid unnecessary manipulations before the assembly.

It is anticipated that any impacts from the assembly method itself will be minimal, if any occur at all. The assembly is designed in such a way that, theoretically, under perfect circumstances, only one long DNA is present in the L-tube after a reaction—the desired DNA product. Under experimental conditions, however, side reactions could occur. They include removal of a nucleotide from the protruding SapI end by an exonuclease activity, a double-stranded break in the DNA as a result of an endonuclease activity, or mechanical shearing. Some of the aberrant products can be removed before transfer to the cell. Nevertheless, some rate of sequence errors will be unavoidable. It is believed that the rate is so low that the isolation of one clone, in most cases, will provide the expected insert sequence.

Another reason for the appearance of aberrant clones is the rearrangement of the structure of the assembled DNA fragment by the cell itself. A reason for this could be the DNA sequence design where signals that promote genomic rearrangements are inadvertently included. These issues can be quickly identified, and addressed.

In embodiments, it is conceivable that one of the more difficult tasks in the approach is to link the first kilo-mer to the particle. In anticipation of this, the particle can be "primed" with short to medium-length DNAs prior to attaching Building Block 1. Priming could be done in several steps as a preparation to the ligation of the Building Blocks to assure that every particle has at least one stretchable DNA molecule attached to it.

Specific embodiments according to the methods of the present invention will now be described in the following examples. The examples are illustrative only, and are not intended to limit the remainder of the disclosure in any way.

The invention is further described in the Appendix that was attached to U.S. Ser. No. 62/296,015, filed Feb. 16, 2016, the contents of which application with appendix are incorporated herein in their entirety.

The invention is further described with respect to the following numbered embodiments:

AA1. A method of performing a reaction involving at least one type of biomolecule or biopolymer in which the structure or properties of said biomolecule or biopolymer are changed due to an application of externally applied force acting on the molecule or biopolymer.

AA2. A method of an AA embodiment, wherein said biomolecule or biopolymer has the random coil structure in solution which is distorted due to an application of externally applied force acting on the biomolecule or biopolymer.

AA3. A method of an AA Embodiment, wherein said externally applied force acting on the biomolecule or biopolymer is due to an electrical or magnetic field, or both.

AA4. A method of an AA embodiment, wherein the reaction comprises linking an end of the first biomolecule or biopolymer to an end of a second biomolecule or biopolymer, and wherein the application of an electrical or magnetic field, or both, renders the linking end of the first biomolecule or biopolymer more accessible to reaction with the linking end of the second.

As indicated by the AA embodiments, the invention is applicable to any number of reaction schemes beyond nucleic acid ligation. As such, any embodiment described with respect to furthering a ligation can be applied with respect to furthering another reaction type. Such methods include coupling single-stranded RNA molecules, where self-association of the RNA may interfere with couplings at the ends or interior sequences.

A1. A method of performing a ligation reaction between a first double stranded DNA fragment and a second, each longer than 1,000 base pairs, in which the random coil structure of molecules belonging to at least one group is distorted due to an application of externally applied force acting on the DNA.

A2. A method of an A Embodiment, wherein the force is due to applying an electrical field.

A3. A method of an A Embodiment, wherein at least one group of DNA molecules is bound to solid phase.

A4. A method of an A Embodiment, wherein said solid phase are nanoparticles, microparticles, or beads.

A5. A method of an A Embodiment, wherein said solid phase are small glass slides (tiles) or tiles made of silicon.

A6. A method of an A Embodiment, wherein the said nanoparticles, microparticles or beads are made of gold.

A7. A method of an A Embodiment, wherein said nanoparticles are coated with an avidin molecule (such as streptavidin) and one group of DNA molecules is labeled with biotin to thereby bind them to the nanoparticles.

A8. A method of an A Embodiment, wherein the said force is due to a hydrodynamic effect caused by the movement of DNA caused by an external force.

A9. A method of an A Embodiment, wherein the external force is due to the magnetic field, and the movement of DNA is due to the attachment of DNA to a magnetic particle.

A10. A method of an A Embodiment, wherein the external force is due to the exposure of the solution containing the molecules being ligated to ultrasound and the movement of DNA is caused by the movement of the solution surrounding the DNA molecule.

A11. A method of assembling DNA molecules longer than 10,000 base pairs comprising multiple ligations of DNA fragments starting with a ligation to a first DNA fragment: wherein (a) in two or more said ligations the added DNA fragment is longer than 1,000 base pairs; and (b) during at least the second of the ligations of clause (a) there is an application of externally applied force acting on one of the DNA molecules to be ligated.

A12. A device to conduct the reaction described in an A Embodiment, such instrument providing means to apply an external force to DNA being ligated.

A13. A device for conducting an A Embodiment, the device capable of generating electric field which is applied to the area in which the ligation reaction is performed to provide the force.

A14. A device for conducting an A Embodiment, wherein the device is capable of performing more than one ligation-mediated synthesis scheme.

AB1. A container (e.g. reaction vessel, or L-tube) to conduct a biochemical reaction comprising built-in or removable electrical part(s) or assembl(ies) for generating electrical field.

AB2. A container (e.g reaction vessel, or L-tube) to conduct a biochemical reaction comprising built-in or removable electrical part(s) or assembl(ies) for generating magnetic field.

AB3. A container (or a reaction vessel, or L-tube) to conduct a biochemical reaction containing built-in or removable electrical part(s) or assembl(ies) for generating electrical and magnetic fields.

AB4. A container of an AB Embodiment, wherein the electrical part(s) or assembl(ies) are configured to create an electrical field effective to make more accessible for ligation a free end a dsDNA of about 10 kb size attached at the other end to a particle, and located within the container, or, where the particle is magnetic, a magnetic field effective to move the particle sufficiently to make the free end more accessible for ligation.

B1. A method of ligating DNA involving a Ninf enzyme (i.e., cleaving outside of its recognition sequence) wherein one DNA fragment is linked (linked meaning sufficiently bound to remain bound throughout the reaction scheme reciting such linking) to solid phase (nanoparticles, magnetic beads, glass beads, flat glass or silicon surface) and the method comprising creating an overhang in a second DNA fragment with the Ninf enzyme and ligating the second DNA fragment to the first via the overhang.

B2. A method of a B Embodiment wherein the restriction activity of said Ninf enzyme is maintained during the ligation reaction.

B3. A method of a B Embodiment wherein the second DNA fragmenthas two cleavage sites for a Ninf enzyme, with one site used to create the overhang, wherein the method further comprises ligating a third DNA fragment with a second distinct overhang created at the second cleavage site, and wherein the Ninf enzyme is present during the ligations.

B4. A method of a B Embodiment, wherein DNA fragments are added sequentially to the ligation reaction mixture and ligated.

B5. A method of an AA or B Embodiment, wherein more than one DNA fragment that is to be ligated is added to the ligation reaction comprising the first DNA fragment at a time.

B6. A method of one of an AA or B Embodiment, wherein the length of the assembled DNA fragments grows exponentially at each assembly step ("pyramidal ligation scheme").

C1. A method of assembling extremely long double stranded DNA comprising: (A) providing, wetted by a reaction composition and attached to a solid support, a DNA strand (double-stranded or single-stranded) having an active selectively ligatible overhang; (B) providing in or adding to the reaction composition a double-stranded DNA strand having a ligation pair of the active selectively ligatible overhang at one end and (i) a second selectively ligatible overhang or (ii) precursor thereof, distinct from the active, at the other end; (C) ligating the two active selectively ligatible overhangs, forming an aggregate DNA strand having an active selectively ligatible overhang that had been the second selectively ligatible overhang; and (D) sequentially repeating steps (B) and (C) until the aggregate DNA strand has formed an extremely long double stranded DNA, wherein in conjunction with one or more of the ligating steps externally applying a force onto the attached double-stranded DNA strand effective to speed said ligation, wherein the external force is so applied in one or more steps where the attached DNA strand has a size of 5 kb or more, wherein two or more of the double-stranded DNA strands of steps (B) are kilo-mers.

C2. The method of a C Embodiment, wherein the external force is one or more of: (a) an electric field; and (b) a hydrodynamic force due to a magnetic force acting on the solid support, which is a magnetic particle.

C3. The method of a C Embodiment, further comprising (E) in conjunction with one or more of the ligating steps sonicating in an amount effective to speed said ligation.

C4. The method of a C Embodiment, further comprising (F) in conjunction with one or more of the ligating steps contacting the attached double stranded DNA in the reaction composition with an amount of DNA-binding protein effective to speed said ligation.

C5. The method of a C Embodiment, wherein the electric field is applied in the ligating steps when the aggregate DNA strand has a size of 20 kb or more [or 10 kb or more, or 5 kb or more].

C6. The method of a C Embodiment, wherein one or more of steps (E) or (F) are applied in the ligating steps once the aggregate DNA strand has a size of 20 kb or more [or 10 kb or more, or 5 kb or more].

C7. The method of a C Embodiment, wherein the solid support comprises one or more particles of dimension of about 4 mm or less [dimension defined as being the larger of L, W and H, or diameter, as relevant].

C8. The method of a C Embodiment, wherein the solid support comprises one or more particles of dimension such that they remain in substantially in suspension for the time scale of a ligation step.

C9. The method of a C Embodiment, further comprising (G) after one or more of the ligating steps replacing the reaction composition and thereby removing free Step (B) polynucleotide from the preceding step (B).

010. The method of a C Embodiment, wherein the particles are magnetic and are retained magnetically during replacements of the reaction composition.

C11. The method of a C Embodiment, wherein in step (A) the solid support comprises two double-stranded DNA strands having distinct active selectively ligatible overhangs, and the subsequent steps (B), (C) and (D) are conducted in parallel with respect to both particle-bound DNA strands, and further comprising ligating, while attached to the support, the resulting separate two extremely long double stranded DNAs.

C12. The method of Embodiment C11, wherein for the synthesis of one of the extremely long double stranded DNAs the overhangs are 5' overhangs, and for the other, 3' overhangs.

D1. A method ligating three or more dsDNA segments at two or more overhanging ligation junctions, wherein the overhanging ligation junctions are defined by non-palindromic overhangs, and wherein each overhanging ligation junction is such that without mismatch error there can be no ligation of the dsDNA segments in an unintended order, the method comprising in a vessel: (1) providing a first dsDNA segment with a defined active said overhang; (2) providing a second dsDNA segment with a ligation pair of the active overhang at one end and a second overhang, distinct from the active, or its precursor at the other end; (3) ligating the active overhang with its ligation pair, forming an aggregate dsDNA having an active overhang that had been the second overhang; and (4) sequentially repeating steps (2) and (3) one or more times, wherein one or more of the following applies, (a) for two or more steps (2) the second dsDNA segment is provided by cleaving in the vessel a vector with one or two Ninf enzymes so as to release the second dsDNA segment with the ligation pair of the active overhang at one end and the second overhang at the other end, wherein the Ninf enzyme(s) recognize sequence including plasmid sequence outside the second dsDNA; and (b) wherein steps (3) following steps (2) that provide dsDNA from vector are conducted in the presence of the respective Ninf enzyme(s).

D2. The method of a D Embodiment, wherein the second dsDNA segments are provided sequentially.

D3. The method of a D Embodiment, wherein two or more the plasmids for sequential steps (2) are added concurrently and the first step (2) relevant with respect to one of these plasmids occurs with all Ninf enzyme(s) relevant to said two plasmids present.

D4. The method of a D Embodiment, wherein the relevant Ninf enzyme(s) for two sequential steps (s) have the cleavage selectivity of Sap I.

E1. A device for assembling extremely long double stranded DNA comprising: a reaction vessel comprising multiple electrodes that can be paired such that they are capable of forming, as voltage is applied across the pairs, an array of fields across the reaction vessel; a voltage source for supplying the voltage; and a controller for serially switching the voltage to such pairs.

E2. The device of an E Embodiment, wherein the device further comprises one or more magnets for applying a magnetic field to the vessel.

E3. The device of an E Embodiment, wherein the magnets comprise electromagnets and the controller operates the magnets in a pattern configured to keep magnetic beads loaded with dsDNA in approximately the same location within the reaction vessel.

F1. A method of assembling DNA comprising providing two distinct kilo-mers (such as >about 5 kb, or 10 kb) attached to a particle, with each kilo-mer having a complementary, non-palindromic overhang; and ligating the distinct kilo-mers in situ to form a ligation product.

F2. The method of an F Embodiment, wherein two sets of such kilo-mers are ligated on the particle to form two distinct ligation products, and further comprising digesting the ligation products to expose for each a particle-attached molecule of substantially [about 20% or more] the ligation product length, with the two having complementary, non-palindromic overhangs, and ligating the distinct molecules in situ to form a second ligation product.

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more. If there are two ranges mentioned, such as about 1 to 10 and about 2 to 5, those of skill will recognize that the implied ranges of 1 to 5 and 2 to 10 are within the invention.

Where a sentence states that its subject is found in embodiments, or in certain embodiments, or in the like, it is applicable to any embodiment in which the subject matter can be logically applied.

This invention described herein is of a DNA assembly method, device, and methods of forming the same. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

REFERENCES

1. Understanding DNA: The molecule and how it works. (2004) Calladine C R, Drew H, Luisi B, Travers A. Academic Press.
2. Zakharova S S, Jesse W, Backendorf C, Egelhaaf S U, Lapp A, van der Maarel (2002) Dimensions of plectonemically supercoiled DNA. Biophys J 83 (2), 1106-1118
3. Dymond J S et al. (2011) Synthetic chromosome arms function in yeast and generate phenotypic diversity by design. Nature 477, 471-476
4. Blake W J et al. (2010) Pairwise selection assembly for sequence-independent construction of long-length DNA. Nucl Acids Res 38, 2594-2602
5. T. Pellegrino T, Sperling R A, Alivisatos A P, Parak W J (2007) Gel electrophoresis of gold-DNA nanoconjugates, J Biomed Biotech Vol 2007, Article ID 26796, 9 pages
6. Yanagida M et al. (1983) Cold Spring Harbor Symp Quant Biol 47, 177-187
7. Robertson R M, Laib S, Smith D E (2006) Diffusion of isolated DNA molecules: dependence on length and topology. Proc Natl Acad Sci USA 103 (19):7310-7314
8. http://www.physiologyweb.com/calculators/diffusion_time_calculator.html
9. Carlson blog, http://www.synthesis.cc/cgi-bin/mt/mt-search.cgi?blog_id=1&tag=Carlson %20Curves, section entitled "Data and references for longest published sDNA" (last accessed on Nov. 22, 2014)
10. Mandecki W, Bolling T J (1988) FokI method of gene synthesis. Gene 68:101-107
11. Mandecki, W., Bolling, T., Shallcross, M. A. and Kavanaugh, T. (1990) Gene synthesis by the FokI method. DNA and Protein Eng. Tech. 2: 33-36
12. Mandecki W, Hayden, M, Shallcross M A and Stotland E (1990) A totally synthetic plasmid for general cloning, expression and mutagenesis in *Escherichia coli*. Gene 94:103-107
13. Mandecki W, Shallcross M A, Kavanaugh, T J (1990) Simple biological assay for the error rate upon cloning of synthetic oligodeoxynucleotides. BioTechniques 9: 56-59

The invention claimed is:

1. A method of assembling a predetermined extremely long double stranded DNA comprising:
   (A) providing, wetted by a reaction composition and attached to a solid support, a DNA strand having an active selectively ligatible overhang;
   (B) providing in or adding to the reaction composition a double-stranded DNA strand having a ligation pair of the active selectively ligatible overhang at one end and (i) a second selectively ligatible overhang or (ii) precursor thereof, distinct from the active, at the other end;
   (C) ligating the two active selectively ligatible overhangs, forming an aggregate DNA strand having an active selectively ligatible overhang that had been the second selectively ligatible overhang; and
   (D) sequentially repeating steps (B) and (C) until the aggregate DNA strand has formed the extremely long double stranded DNA, wherein incorporated segments of DNA from the DNA strands of steps (A) and (B) are unique with respect to one another,
   wherein in conjunction with one or more of the ligating steps externally applying a force onto the attached double-stranded DNA strand effective to speed said ligation, wherein the external force is one or more of: (a) an electric field; and (b) a hydrodynamic force due to a magnetic force acting on the solid support, which is a magnetic particle,
   wherein for two or more of steps (B) the double-stranded DNA strand of that step is sized from about 1 kb to about 40 kb,
   wherein the ligation enhancing external force is so applied in any steps (C), and at least one or more steps (C), where the attached, aggregate DNA strand has a size of 20 kb or more or the double-stranded DNA strand of steps the preceding step (B) is sized from about 1 kb to about 40 kb, and
   wherein the extremely long double stranded DNA obtained from steps (A) to (D) and without PCR is in an amount of 1 ng more.

2. The method of claim 1, further comprising
   (E) in conjunction with one or more of the ligating steps sonicating in an amount effective to speed said ligation.

3. The method of claim 2, wherein step (E) is applied in the ligating steps once the aggregate DNA strand has a size of 20 kb or more.

4. The method of claim 1, further comprising (F) in conjunction with one or more of the ligating steps contacting the attached double stranded DNA in the reaction composition with an amount of DNA-binding protein effective to speed said ligation.

5. The method of claim 4, wherein step (F) is applied in the ligating steps once the aggregate DNA strand has a size of 20 kb or more.

6. The method of claim 1, wherein the solid support comprises one or more particles of dimension of about 4 mm or less.

7. The method of claim 1, wherein the solid support comprises one or more particles of dimension such that they remain in substantially in suspension for the time scale of a ligation step.

8. The method of claim 1, further comprising (G) after one or more of the ligating steps replacing the reaction composition and thereby removing free Step (B) polynucleotide from the preceding step (B).

9. The method of claim 8, wherein the particles are magnetic and are retained magnetically during replacements of the reaction composition.

10. The method of claim 1, wherein in step (A) the solid support comprises two double-stranded DNA strands having distinct active selectively ligatable overhangs, and the subsequent steps (B), (C) and (D) are conducted in parallel with respect to both particle-bound DNA strands, and further comprising ligating, while attached to the support, the resulting separate two extremely long double stranded DNAs.

11. The method of claim 10, wherein for the synthesis of one of the extremely long double stranded DNAs the overhangs are 5' overhangs, and for the other, 3' overhangs.

12. The method of claim 1, wherein the external force comprises an electric field; and (b) a hydrodynamic force due to a magnetic force acting on the solid support, which is a magnetic particle.

13. The method of claim 1, wherein the external force comprises a hydrodynamic force due to a magnetic force acting on the solid support, which is a magnetic particle.

\* \* \* \* \*